United States Patent [19]

Sansanelli

[11] 3,935,956
[45] Feb. 3, 1976

[54] CONTAINER AND HANGER CLIP THEREFOR

[75] Inventor: Edward Sansanelli, Hasbrouck Heights, N.J.

[73] Assignee: Airwick Industries, Inc., Teterboro, N.J.

[22] Filed: Oct. 2, 1974

[21] Appl. No.: 511,185

[52] U.S. Cl............................. 215/100 R; 248/359
[51] Int. Cl.².......................................... B65D 25/22
[58] Field of Search......... 248/360, 359; 215/100 R; 222/181

[56] References Cited
UNITED STATES PATENTS

| | | | |
|---|---|---|---|
| 1,328,162 | 1/1920 | Hecht | 248/360 |
| 3,627,177 | 12/1971 | Marcus | 222/181 |

*Primary Examiner*—Donald F. Norton
*Attorney, Agent, or Firm*—Curtis, Morris & Safford

[57] ABSTRACT

A container and hanging device therefor is disclosed wherein the container has a support wall having the hanging device mounted thereon and a contiguous side wall extending from the support wall. The container is adapted to be supported on a support member, for example the inside of a toilet flush tank, by the hanging device, which consists of a generally U-shaped clip having a bight portion and a pair of spaced legs, which clip is pivotally mounted on the support wall of the container for movement between a storage position, wherein the bight portion of the clip is adjacent and parallel to the side wall of the container, and a support position, wherein the bight portion of the clip extends parallel to the support wall and at least a part of the bight portion extends beyond the container so that one of the legs of the clip is in spaced relation to the side wall of the container for receiving therebetween the support member or wall of the flush tank so as to suspend the container therefrom.

13 Claims, 5 Drawing Figures

CONTAINER AND HANGER CLIP THEREFOR

The present invention relates to a combination container and hanging device, and more particularly to a container for use as a flush tank accessory.

There has recently developed a demand for dispensing devices which will dispense into the flush tank of a toilet a detergent or room freshener. Such dispensers are typically suspended in the flush tank by a clip arrangement which mounts the dispensing container on a wall of the tank. Since such dispensers are typically used by mechanically unskilled purchasers, such as housewives, it is extremely desirable that the hanging device therefor be easy to use. Obviously, the hanging device should also be relatively inexpensive so that the entire dispensing container and hanging device combination can be discarded when the detergent or room freshener in the container is depleted.

Although a number of hanging devices for dispensing containers of this type have previously been proposed, it has been found that they are not entirely satisfactory in use. Typically, the hanger consists of a thin metal sheet or tab, secured to the container, which can be easily bent or disformed, and which may not have sufficient strength to support a completely filled container in the flush tank. If these metal hanging devices become bent or disfigured, they may not be able to support the container in the desired predetermined operating position necessary to allow the dispensing valve or the like in the container to operate satisfactorily, and may even prevent the device from being suspended in the flush tank at all. Moreover, it is possible with these thin metal hanging devices that the user can become injured from sharp metal edges or burrs which may be formed thereon.

Accordingly, it is an object of the present invention to support a dispensing device in a flush tank by means of a relatively strong and safe hanging member or clip.

Another object of the present invention is to provide a hanging clip for a dispensing container which is relatively inexpensive and convenient to manufacture.

A further object of the present invention is to provide a combination container and hanging device therefor which can be easily used by the housewife.

A still further object of the present invention is to provide a container and hanging device therefor which is durable in use.

A still further object of the present invention is to provide a container and hanging device therefor, which hanging device has sufficient strength to support the container and is compact with the container so as to allow ready packaging thereof.

In accordance with an aspect of the present invention, a container and hanging device therefor are provided in which the container has a bottom wall and a side wall adjacent to and extending from the bottom wall, with the hanging device or clip being pivotally mounted on the bottom wall for engagement with a support member or wall of a flush tank from which the container can be suspended. The support clip has a generally U-shaped configuration and includes a pair of spaced legs and a bight portion which extends therebetween. Pivot means pivotally mount the clip on the bottom wall of the container adjacent the junction of the bottom wall with the side wall thereof to allow movement of the clip between a storage position, wherein the bight portion of the clip is adjacent and parallel to the side wall of the container in a compact arrangement, and a support position, wherein the bight portion of the clip extends parallel to the bottom wall of the container with at least a part of the bight portion extending beyond the side wall. In this position one leg of the clip is located in spaced relation to the side wall, thereby to allow the support member or wall of the flush tank to be received between the side wall and the leg of the clip so that the container can be suspended in the tank. The other leg of the clip overlies the bottom wall and prevents pivotal movement of the clip beyond the support position thereof so that the container is rigidly held in a fixed position in the tank.

The above and other objects, features, and advantages of this invention will be apparent from the following detailed description of an illustrative embodiment thereof, which is to be read in connection with the accompanying drawing, wherein.

Figure 1:
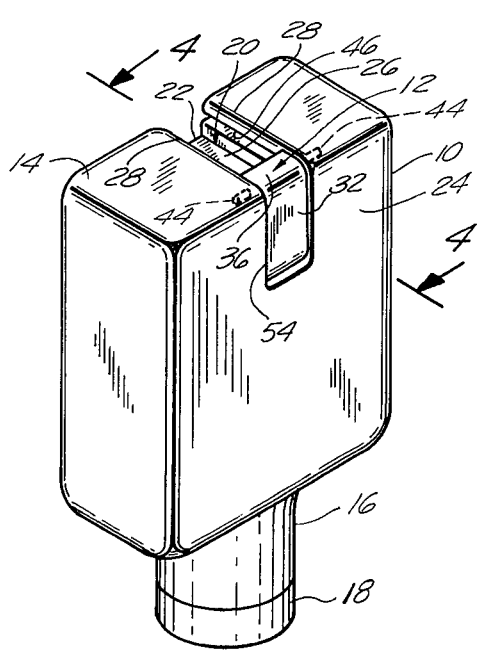
FIG. 1 is a perspective view of a container and hanging device combination constructed in accordance with the present invention.
Figure 2:
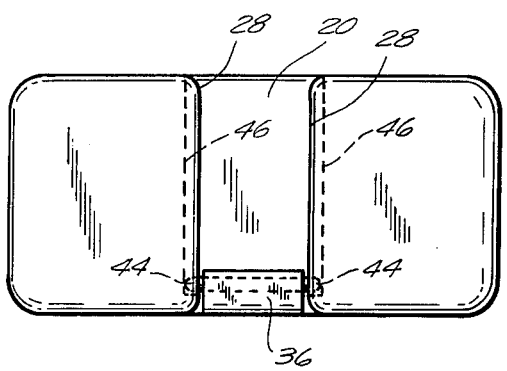
FIG. 2 is a plan view of the bottom wall of the container and clip shown in FIG. 1, with the clip in its storage position.
Figure 5:
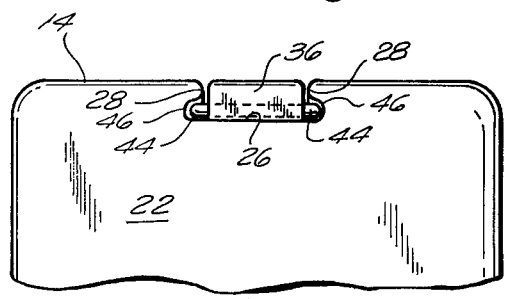
FIG. 5 is a partial elevational view, similar to FIG. 3, showing the side of the container opposite to that illustrated in FIG. 3.

Referring now to the drawings in detail, and particularly to FIG. 1 thereof, it will be seen that container 10 constructed in accordance with the present invention includes hanging clip 12 mounted on bottom wall 14 of the container in order to suspend or support the container on a wall of a flush tank. The container can be formed in any desirable shape, for example of a suitable plastic or glass material, and is provided with a plurality of side walls extending from bottom wall 14 thereof to neck 16. The neck of the container is closed by cap 18 which includes a suitable dispensing mechanism, of any convenient known construction, which will dispense a liquid detergent or room freshener from the container into the water of the flush tank. The specific dispensing arrangement in cap 18 can be of any of the dispensing arrangements known in the art: the dispensing mechanism, per se, does not form part of this invention.

Figure 3:
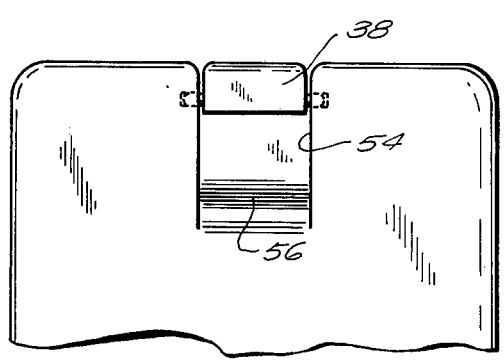
FIG. 3 is a partial elevational view of the container and clip assembly of FIG. 1, with the clip in its support position.

Bottom wall 14 of container 10 has recess 20 formed therein which extends entirely across the bottom wall from rear wall 22 of the container to front wall 24 thereof. Recess 20 has a width that is slightly greater than that of clip 12, and includes base 26 and a pair of spaced side walls 28. Clip 12 is pivotally mounted in recess 20, as described more fully hereinafter, for movement from a first, storage position in FIG. 1 (also illustrated in phantom lines in FIG. 4) wherein it is located adjacent side wall 24 of the container to a second, support position in FIG. 3 (illustrated in solid lines in FIG. 4) wherein it can engage a support member, e.g. side wall 30 of a flush tank for a toilet, in order to suspend the container within the flush tank.

Clip 12 is preferably formed of a plastic material and has a generally U-shaped configuration, in longitudinal section, including bight portion 32 and a pair of spaced depending legs 36, 38 respectively. The clip is pivotally supported in recess 20 by pivot pin 40 which is integrally formed therewith on the end of third leg 42 located between the legs 36, 38. Leg 42 and pivot pin 40 are preferentially located closer to leg 36 of the clip.

Pivot pin 40 has free ends 44 which are received in slots 46 formed in side wall 28 of recess 20. The slots 46 extend from rear wall 22 of container 10 along side walls 28 to abutment end portions 48 which are located adjacent junction 50 between bottom wall 14 and side wall 24 of the container. By this arrangement, clip 12 is conveniently inserted by the manufacturer on container 10 by simply inserting ends 44 of the pivot pin in the opened ends of slots 46, adjacent the rear wall 22 of the container, and sliding the entire clip toward front wall 24 until the ends of the pivot pin engage abutment ends 48 of the slots.

Figure 4:
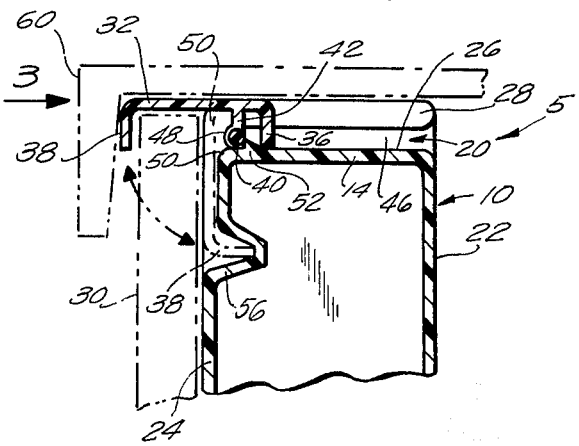
FIG. 4 is a partial sectional view taken along line 4—4 of FIG. 1 showing in phantom lines portions of a flush tank in which the assembly can be mounted.

In order to retain pivot pin 40 adjacent to the abutment ends of the slots, bottom wall 14 of container 10 is provided with boss or enlargement 52 that extends across base 26 of recess 20, between slots 46, but in spaced relation to the abutment ends thereof. Since either or both of container 10 and clip 12 are conveniently formed of a somewhat resilient plastic material, it will be apparent that as pivot pin 40 is inserted into container 10, it will move across boss 52 into the space between the boss abutment ends 48 of slots 46. Due to the cam shaped configuration of boss 52, as seen in FIG. 4, it will be apparent that this movement will be accommodated by the boss, particularly because of the resilient materials of which the elements are formed, but that rearward movement of the pivot pin in the slot towards rear wall 22, after it has achieved the position in FIG. 4, will be prevented by the boss. Thus the clip is held in a fixed position in slots 46, but it is permitted to pivot therein.

Front wall 24 of container 10 has recess 54 formed therein which is substantially complementary to the configuration of clip 12. That is, recess 54 includes major indentation 56 which is adapted to receive leg 38 of clip 12 when the clip is in its storage position (shown in phantom lines in FIG. 4), while the remainder of recess 56 receives the bight portion 32 of the clip so that the clip is substantially flush with the surface of side wall 24 when in its storage position.

Preferably the combination container and clip assembly of the present invention is packaged and shipped with clip 12 in the storage position, adjacent front wall 24 of the container. When the purchaser wishes to mount the container or dispensing device in a flush tank, clip 12 is pivoted in a generally clockwise direction, as seen in FIG. 4, from its storage position to its support position. Pivotal movement of the clip in this direction about pivot pin 40 is limited upon engagement of leg 36 of the clip with base 26 of slot 20. Thus leg 36 of the clip forms a stop means for the clip structure. In this position, a portion of bight 32 of the clip extends beyond container 10, so that leg 38 is located in spaced relation to the front wall 24 of the container. The clip is dimensioned so that the space between leg 34 and wall 24, in this position of the clip, is sufficient to accommodate the edge of wall 30 of a conventional flush tank therebetween. When the clip is placed on flush tank wall 30 in this manner, container 10 is rigidly supported in the tank by the engagement of pivot pin 40 in slots 46 and the engagement of leg 36 of the clip against the base of recess 20. Thereafter, the user can then replace top 60 of the flush tank on tank wall 30.

It will be appreciated that the invention provides a relatively simple hanging device and container structure for use as a dispenser in a flush tank. Hanging clip 12 of the invention provides a durable and sturdy support for the container which is safe to use and relatively inexpensive to manufacture. Since all that is required to place the clip in its operative position is a simple pivotal movement, the device is easily used by a housewife.

Although an illustrative embodiment of the present invention has been described herein with reference to the accompanying drawing, it is to be understood that this invention is not limited to that precise embodiment but that various changes and modifications may be effected therein by one skilled in the art without departing from the scope or spirit of this invention.

What is claimed is:

1. An article of manufacture comprising, in combination, a hollow container having a support wall and a side wall extending angularly therefrom, a generally U-shaped clip having a bight portion and a pair of spaced legs; and means for pivotally mounting said clip on said support wall for movement between a storage position wherein the bight portion of the clip is adjacent and parallel to said side wall and a support position wherein the bight portion of the clip extends parallel to said support wall and at least part of said bight portion extends beyond the container for supportive engagement with a support member from which the container can be suspended; said pivotal mounting means being operatively connected to the bight portion of said clip between the legs thereof whereby, in said support position of the clip, one of said legs is located in spaced relation to the container and the free end of the other of said legs is engaged with said support wall, thereby to provide a stop limiting pivotal movement of the clip.

2. The article as defined in claim 1 wherein said pivotal mounting means comprise a pivot pin integrally formed with said clip and means on said support wall for retaining the pivot pin thereon.

3. The article as defined in claim 2 wherein said side wall has a recess formed therein for receiving the bight portion and said one leg of the clip in the storage position thereof with said bight portion extending substantially flush to said side wall.

4. The article as defined in claim 1 wherein said side wall has a recess formed therein for receiving the bight portion and said one leg of the clip in the storage position thereof with said bight portion extending substantially flush to said side wall.

5. The article as defined in claim 1 wherein said pivotal mounting means include a pivot pin operatively connected to said bight portion of the clip between the legs thereof and having a pair of spaced free end portions; said support wall having an elongated recess formed therein including a pair of spaced slots respectively receiving the free ends of said pivot pin, and means in said recess for maintaining said pivot pin in a relatively fixed position with respect to the recess while allowing pivotal movement thereof.

6. The article as defined in claim 5 wherein said maintaining means comprise a boss extending upwardly from the base of said recess.

7. An article of manufacture comprising a container having a bottom wall and a side wall adjacent to and extending angularly from said bottom wall, and a hanger clip pivotally mounted on the bottom wall of said container for engagement with a support member from which the container can be suspended; said support clip having a generally U-shaped configuration including a pair of spaced legs and a bight portion extending therebetween; and pivot means for pivotally mounting said clip on said bottom wall adjacent its junction with said side wall for movement between a storage position wherein the bight portion of the clip is adjacent and parallel to said side wall and a support position wherein the bight portion of the clip extends parallel to said bottom wall and at least a part of the bight portion extends beyond said side wall with one leg of said clip in spaced relation to the side wall to receive a support member therebetween whereby said container may be suspended from the support member; said pivot means comprising a pivot pin operatively connected to the bight portion of said clip between the legs thereof whereby, in the support position of the clip, the other of said clip legs is engaged with said bottom wall to provide a stop limiting pivotal movement of said clip beyond said support position.

8. The article as defined in claim 7 wherein said pivot pin extends transversely of said bight portion of the clip and includes a pair of free ends; said bottom wall having a pair of elongated spaced slots formed therein including abutment end portions adjacent the junction of the bottom wall and the side wall; and means for retaining said pin in said slots adjacent the abutment end portions thereof.

9. The article as defined in claim 8 wherein said slots extend across said bottom wall from their abutment ends to free open ends through which the ends of said pivot pin are inserted.

10. The article as defined in claim 9 wherein said retaining means comprise a boss formed on said bottom wall between said slots adjacent to and spaced slightly rearward from the abutment ends thereof; at least one of said pivot pins and boss being formed of a resilient material, whereby the pivot pin can be moved in said slots across the boss into engagement with said abutment ends of the slots to be held there by the boss.

11. The article as defined in claim 10 wherein said bottom wall has an elongated recess formed therein extending entirely across the bottom wall from said side wall and having a base and opposed parallel sides, said slots being formed in the sides of said recess and said boss being located in the base thereof.

12. The article as defined in claim 11 wherein said slot has a depth substantially equal to the height of the clip legs, whereby in the support position of the clip the bight portion thereof is substantially flush with said bottom wall.

13. The article as defined in claim 12 wherein said side wall has a recess formed therein for receiving the bight portion and said one leg of the clip in the storage position thereof with said bight portion extending substantially flush to said side wall.

* * * * *